United States Patent [19]
Connors

[11] Patent Number: 5,153,495
[45] Date of Patent: Oct. 6, 1992

[54] CONVERTIBLE BATTERY HANDLE

[75] Inventor: John D. Connors, Auburn, N.Y.

[73] Assignee: Welch Allyn, Inc., Skaneateles Falls, N.Y.

[21] Appl. No.: 763,143

[22] Filed: Sep. 20, 1991

[51] Int. Cl.[5] .......................... H02J 7/00; F21L 1/00; H01M 10/46

[52] U.S. Cl. ......................................... 320/2; 320/15; 362/183

[58] Field of Search ...................... 320/2, 15; 362/183

[56] References Cited

U.S. PATENT DOCUMENTS

| | | |
|---|---|---|
| 3,070,748 | 12/1962 | Worobey et al. ............. 320/2 X |
| 3,096,941 | 1/1960 | Miller . |
| 3,201,742 | 8/1965 | English . |
| 3,281,637 | 9/1963 | Hultquist . |
| 3,506,902 | 4/1970 | Sullivan ......................... 320/2 |
| 4,147,163 | 4/1979 | Newman et al. . |
| 4,382,219 | 5/1983 | Heine et al. . |
| 4,602,202 | 7/1986 | Mundschenk et al. .......... 320/2 |
| 4,628,242 | 12/1986 | Scholefield .................... 320/2 |
| 4,782,432 | 11/1988 | Coffman . |

*Primary Examiner*—R. J. Hickey
*Attorney, Agent, or Firm*—Wall and Roehrig

[57] ABSTRACT

A convertible battery handle is provided in which an extended end cap contains a drive spring electrically insulated from the battery circuits to physically hold the rechargeable battery pack or non-rechargeable battery cells in proper position and a coaxial helical spring electrically connected into the battery circuit. The helical spring has a length insufficient to make electrical contact when the handle is utilized with a rechargeable battery pack, but when a pair of non-rechargeable dry cells are positioned in the handle the electrical circuit is completed through the spring. A safety diode is placed in the series with the electrical circuit for the non-rechargeable cells to prevent inadvertent charging of the cells.

8 Claims, 1 Drawing Sheet

CONVERTIBLE BATTERY HANDLE

BACKGROUND OF THE INVENTION

This invention relates to battery handles for diagnostic medical instruments and apparatus and more particularly to a convertible rechargeable battery handle which can accept both a rechargeable battery pack and standard non-rechargeable cells for providing power to a medical instrument.

In recent years diagnostic medical instruments in general and particularly instruments such as ophthalmoscopes, otoscopes, retinoscopes, transilluminators and the like have been provided with interchangeable and rechargeable battery handles so that the instruments can be used free of any cords or other attachments for supplying the necessary illumination. This has required, of course, that the batteries be periodically recharged and this has been accomplished by various means such as placing the handle in a recharging fixture, disconnecting the instrument head from the handle and plugging the handle into a wall socket and similar means.

These battery handles have proved to be very satisfactory as long as the physician remembers to plug them into a charging fixture when not in use and there is no power failure at the time the battery handle needs recharging. Various systems have been proposed in the past to allow use of standard non-rechargeable cells in a rechargeable battery handle when the battery pack is discharged. In U.S. Pat. No. 4,147,163 an apparatus is shown where the rechargeable cell is longer than the non-rechargeable cells and a spring biased moveable contact is provided to make contact with the charging circuit when a rechargeable battery is installed. The handle can then be inserted in a charging unit to recharge the battery pack. The non-rechargeable cells when installed in the handle, and the contact, are spring biased out of the charging circuit so as to prevent inadvertent charging of the non-rechargeable cells.

U.S. Pat. No. 4,382,219 shows a movable spring biased contact pin in the charging fixture that is adapted to engage a rechargeable battery pack terminal through an aperture in the handle when the handle is positioned in the charger. A stop and flange are provided to prevent the contact pin from making contact with non-rechargeable batteries installed in the handle. In this system the rechargeable battery must have a length equal to or greater than the non-rechargeable cells. Non-rechargeable cells are held in place in the handle by a second spring which acts both as a contact and drive spring.

Neither of the configurations shown would work where the rechargeable battery pack is shorter than the desired nonrechargeable replacement cells. The present invention addresses this problem for those situations where the non-rechargeable cells are longer than the rechargeable battery pack by providing an end cap closure for converting the conventional rechargeable battery handle to a standard non-rechargeable cell battery handle configuration. The present invention has no moving contacts, requires no moving parts, and uses a diode for preventing charging of the non-rechargeable cells. The deflection of the drive spring permits electrical contact through the coaxial spring without movement of any other contacts in a simpler and more economical fashion.

OBJECTS AND SUMMARY OF THE INVENTION

Accordingly, it is an object of the present invention to provide a convertible rechargeable battery handle that overcomes the limitations of the prior art.

It is another object of the present invention to provide an elongated end cap for a rechargeable battery handle to convert it to a universal battery handle that will accept a rechargeable battery pack or conventional non-rechargeable batteries as the source of power for the instrument head.

It is another object of the present invention to provide an end cap closure for a rechargeable battery pack handle that will allow conversion to non-rechargeable cell battery operation with means for preventing an inadvertent charging of non-rechargeable cells when positioned in the handle.

These and further objects and advantages are attained in one embodiment of the invention by providing, as a replacement for the standard end cap of a rechargeable battery handle, an elongated end cap in which is positioned an electrically insulated mechanical drive spring for positioning batteries within the handle end cap, together with a second coaxially mounted helical spring having a length sufficient to electrically connect a pair of non-rechargeable cells into the operating circuit, but too short to connect the rechargeable battery pack into the electrical circuit. A diode is placed in the contact circuit of the second spring to prevent accidental charging of the non-rechargeable cells.

BRIEF DESCRIPTION OF THE DRAWINGS

Additional features and advantages of the present invention will appear from the following description of a preferred embodiment which is shown in the accompanying drawings in which.

DETAILED DESCRIPTION OF THE PREFERRED EMBODIMENT

Figure 1:
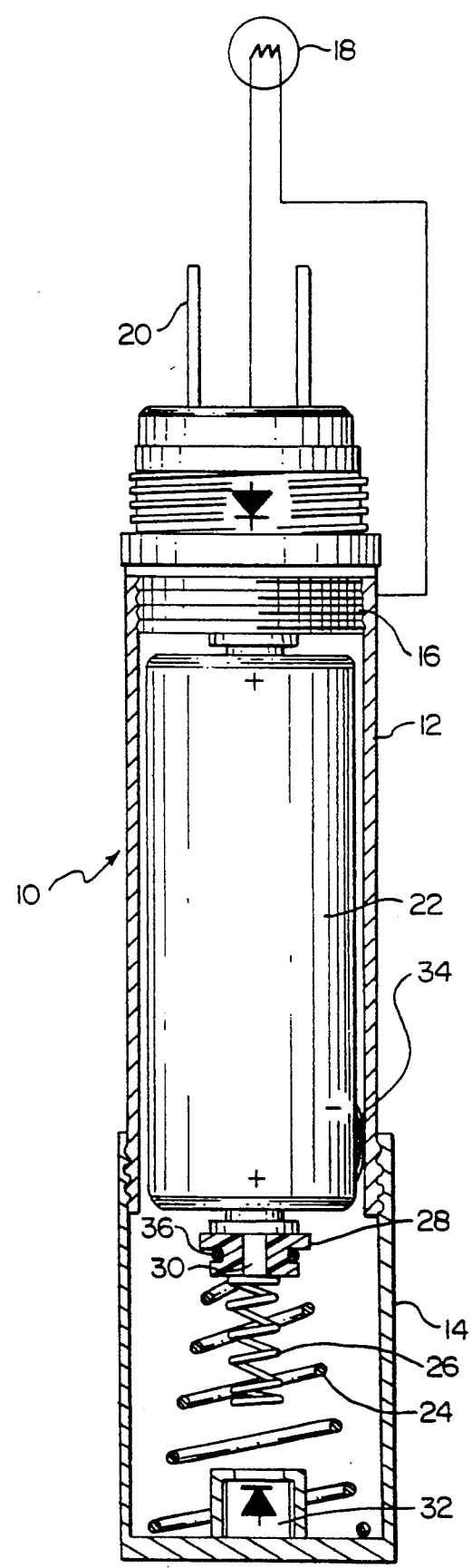
FIG. 1 is a cross sectional view of a rechargeable battery handle according to the present invention with a rechargeable battery pack installed therein.

Referring now to FIG. 1, the convertible battery handle 10 according to the present invention comprises a tubular main body portion 12 open at one end. The open end is closed by an elongated cap 14 and the other end of body 12 has positioned therein a charging module 16 and bayonet contact means 20 for connecting the battery handle to a charging circuit such as a wall socket or to an instrument head shown schematically at 18.

Positioned within the elongated cylindrical body of the convertible handle 10 is a rechargeable nickel-cadmium battery pack 22 having positive contacts at each end and a ground spring contact 34 along one side. The battery pack 22 is positioned within the housing 12 by a drive spring 24 which extends between the inside bottom of the cap 14 to an insulating bushing 28. A slot 36 in bushing 28 receives the upper end of spring 24. Bushing 28 is thus spring urged against the end of the battery pack and physically holds it in the proper operating position within the convertible handle. Spring 24 is electrically insulated from the battery pack operating circuits by the bushing 28. Mounted in the center of bushing 28 is an electrical contact ferrule 30 which has a button surface at the top and is electrically and mechanically connected to a spring 26 axially aligned within the spring 24. Spring 26 is shorter in length than the spring 24 and is electrically insulated therefrom.

The casing 12 and end cap 14 are generally made of an electrically conducting material such as metal which acts as the ground for the instrument. Mounted in the bottom of the end cap 14 is a diode 32 which is in electrical contact with the end cap and which is adapted to electrically and mechanically engage the lower end of spring 26 when a pair of non-rechargeable cells 38 are mounted in the handle 10 rather than the battery pack 22.

Figure 2:
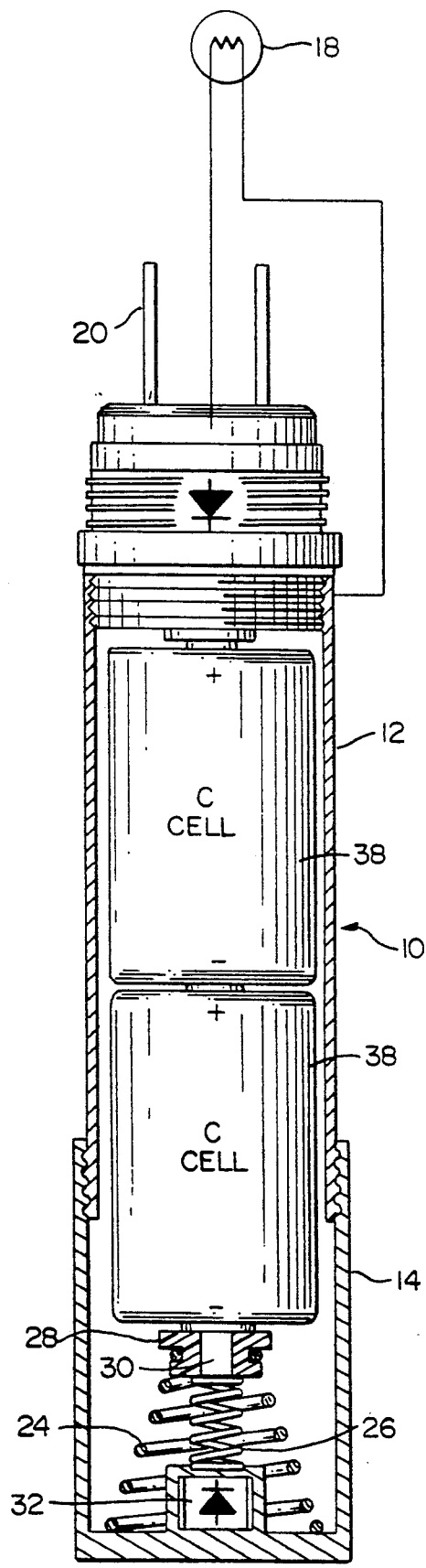
FIG. 2 is a view similar to FIG. 1 showing a pair of non-rechargeable cells installed in place of the battery pack.

Referring now to FIG. 2, the handle 10 is shown with two non-rechargeable cells 38 installed in the handle in place of the battery pack 22. These cells, for example, may be two standard "C" size dry cells. In this configuration, it will be seen that the spring 26 now makes electrical contact with the diode 32 and with the bottom of the lower cell 38 completing the ground connection for the non-rechargeable cells to the cap 14 and outer shell 12. The drive spring 24 still provides the mechanical force to maintain the cells 38 in the proper operating position within the handle 10 in similar fashion to the positioning of the battery pack 22.

The electrical discharge circuit in FIG. 1 is from the upper positive terminal (+) of the battery pack 22 through the light bulb of the instrument head 18 to the top of the casing 12 as shown diagrammatically. From casing 12 the circuit is completed through the ground spring 34 to the negative side of the battery pack 22. There is no electrical connection with the lower positive contact of the battery pack 22 since spring 26 does not touch the end cap 14 or the diode 32 and spring 24 is electrically insulated from the battery pack 22.

In FIG. 2, the electrical circuit starting at the positive (+) end of the upper cell 38 extends through the instrument head as shown diagrammatically at 18 and then back to the top of the casing 12 as in FIG. 1. The circuit continues through the casing 12, through the end cap 14 to the diode 32, and thence to the spring 26 and the contact ferrule 30 to the bottom of the lower cell 38 which is the negative or ground side of the nonrechargeable cells, thus completing the circuit.

In the configuration of FIG. 1, the charging circuit for battery pack 22 is from one of the blades of the bayonet contact 20 through the positive terminal of the battery pack at the upper end through the battery pack and then through the ground contact spring 34 to the casing of the handle 10 and back to the other contact blade. In the configuration of FIG. 2 should the rechargeable handle 10 be accidentally plugged into a wall socket, the non-rechargeable cells would not be charged or blown up because the diode 32 would block the charging circuit. If handle 10 is inadvertently plugged into a wall socket, the circuit would start out the same through one of the blades 20 of the charging module 16 through the plus side of the top cell 38 to the bottom cell 38, down through the ferrule 30 and spring 26 to the diode 32. As can be seen in FIG. 2, the diode would prevent any significant conduction of current to the casing which would prevent completion of the charging module circuit.

It is thus apparent that I have provided a convertible battery handle for use with either a rechargeable battery pack or non-rechargeable cells such as a pair of conventional dry cells. The battery handle and extended end cap can be used in the normal rechargeable mode without any change and should power fail or the battery pack, for some reason not be charged, standard dry cells can be inserted in the handle which is then fully operable for emergency use.

While this invention has been explained with reference to the structure disclosed herein, it is not confined to the details as set forth and this application is intended to cover any modifications and changes as may come within the scope of the following claims.

What is claimed is:

1. A closure device for a battery handle that is arranged to accept either a rechargeable battery having a top wall terminal and a side wall terminal of different polarities or non-rechargeable batteries having terminals of different polarities in the top and bottom walls thereof, said batteries being used as a source of power for an instrument attached thereto, the improvement comprising:
   end cap means removably attached to a battery handle capable of accepting either a rechargeable battery or non-rechargeable batteries;
   a spring means mounted in said end cap extending upwardly into the handle to mechanically position batteries within the handle;
   a contact means mounted in said spring means that is electrically isolated from said spring means and is arranged to contact a battery positioned in the handle;
   a flexible conductive member connected to said contact means that extends downwardly therefrom;
   diode means mounted in said end cap beneath the flexible member that is coupled to a battery circuit having means for coupling the diode to the flexible member when non-rechargeable cells are positioned in the handle to permit current to flow out of said batteries and to prevent current form flowing into said batteries;
   means for uncoupling said flexible member from said diode means when a rechargeable battery is positioned in said handle;
   and the length of said flexible member being chosen so that upon replacement of a rechargeable battery with non-rechargeable batteries said flexible member will make electrical contact with said diode to complete an operating circuit for said battery handle.

2. A closure device according to claim 1 wherein said spring means is chosen with sufficient elasticity and spring force to maintain either a rechargeable battery or non-rechargeable batteries in an operative electrical contact position within said handle to which it is attached.

3. A closure device according to claim 1 wherein said contact means is seated in a nonconducting bushing having an annular groove in its outer circumference;
   said spring means comprising a conical shaped compression spring; and
   the upper turn of said spring is mounted in said groove so as to hold said bushing centered in one end of said end cap.

4. A closure device according to claim 1 wherein said diode means is oriented to prevent accidental charging of nonrechargeable cells and accidental discharge of a rechargeable battery pack placed in an inverted position in said battery handle while permitting normal operation of said batteries.

5. A closure device according to claim 1 wherein said end cap has an axial length sufficient to accommodate non-rechargeable cells having an overall length greater than that of a rechargeable battery pack.

6. A convertible rechargeable battery handle for use in powering a hand-held instrument, said handle being arranged to accept either a rechargeable battery pack having a top terminal and a side terminal of different polarities or non-rechargeable battery cells having top and bottom terminals of different polarities and an overall length that is greater than that of the rechargeable battery, said battery handle including,
- a body member for housing, either a rechargeable battery pack or non-rechargeable battery cells that is closed at one end by a removable end cap and at the other end by a plug-in adaptor means.
- said body member further including circuit means to permit charging of the rechargeable battery pack and providing power to an instrument,
- a first spring means mounted in the end cap electrically isolated from said circuit means for mechanically positioning either a rechargeable battery pack or non-rechargeable battery cells within said body member,
- a second spring means mounted in the end cap that is electrically isolated from said first spring means, said second spring means being arranged so that it will not contact a terminal on said rechargeable battery pack positioned in said body member and will make contact with one of the terminals of said nonrechargeable battery cells positioned in the body member, and
- means associated with said last mentioned means to permit current to flow out of said cells and prevent the flow of current into said cells.

7. A convertible battery handle according to claim 6 wherein said plug-in adaptor means includes means for operatively engaging a source of charging power or an instrument head to provide power thereto.

8. A convertible battery handle according to claim 6 that further includes an insulating bushing positioned in the upper end of said first spring means;
- a contact ferrule mounted in said bushing that is electrically isolated from said first spring means; and
- said second spring means being mechanically and electrically fixed on said ferrule.

* * * * *